US00PP17577P3

(12) United States Plant Patent
Schlueter

(10) Patent No.: US PP17,577 P3
(45) Date of Patent: Apr. 10, 2007

(54) ***HIBISCUS ROSA-SINENSIS* PLANT NAMED 'ENLIGHTENMENT'**

(50) Latin Name: *Hibiscus rosa-sinensis*
Varietal Denomination: ENLIGHTENMENT

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 40 days.

(21) Appl. No.: 11/207,517

(22) Filed: Aug. 19, 2005

(65) Prior Publication Data

US 2007/0044189 P1 Feb. 22, 2007

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
(74) *Attorney, Agent, or Firm*—Christie, Parker & Hale, LLP

(57) ABSTRACT

A new and distinct cultivar of *Hibiscus* plant named 'ENLIGHTENMENT', characterized by a large, ruffled, multicolored flower with a pink center, an orange halo and yellow edges, with white flecks throughout the center. 'ENLIGHTENMENT' is a free flowering plant with an upright, compact habit, and glossy, dark green foliage.

4 Drawing Sheets

Botanical classification: *Hibiscus rosa-sinensis 'ENLIGHTENMENT'*.

Varietal denomination: The new plant has the varietal denomination 'ENLIGHTENMENT'.

BACKGROUND OF THE INVENTION

The present invention relates to a new and distinct cultivar of *Hibiscus,* botanically known as *Hibiscus rosa-sinensis* and hereinafter referred to by the cultivar name 'ENLIGHTENMENT'.

The genus *Hibiscus* comprises about 250 species of herbs, shrubs and trees in warm temperate and tropical regions; with leaves usually simple, mostly palmately veined, lobed or parted; flowers are mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves grow to 6-inches in length, and are ovate, usually serrate, mostly glossy green. Flowers are solitary in upper leaf axils.

The new *Hibiscus* is a product of a planned breeding program conducted by the Inventor in Webster, Tex. The objective of the program was to create new *Hibiscus* selections with improved bloom quality, color and floriferousness. A further objective was to produce plants that can be commercially produced on their own root systems, with improved plant habit, with regard to vigor and postproduction longevity.

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;

2. Healthy dark green foliage;
3. Vigorous growth habit;
4. Large ruffled multicolored flower with a pink center, an orange halo and yellow edges, with white flecks throughout the center; and
5. Free flowering.

SUMMARY OF THE INVENTION

The cultivar 'ENLIGHTENMENT' has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'ENLIGHTENMENT'. These characteristics in combination distinguish 'ENLIGHTENMENT' as a new and distinct cultivar:

1. Upright, compact symmetrical plant habit that is suitable for container production
2. Healthy dark green foliage.
3. Vigorous growth habit.
4. Large ruffled multicolored flower with a pink center, an orange halo and yellow edges, with white flecks throughout the center.
5. Free flowering.

Asexual reproduction of the new variety by stem cuttings, performed in Webster, Tex. and Houston, Tex., have confirmed that the distinctive characteristics of the new variety are stable and transmitted to succeeding generations, and the new variety reproduces true to type.

COMPARISON WITH PARENTS AND OTHER CULTIVARS

'ENLIGHTENMENT' is distinguished from its female parent 'Georgia's Pearl' (not patented) by its flower color, the flower of 'ENLIGHTENMENT' having more yellow and less orange than that of 'Georgia's Pearl'. 'ENLIGHTENMENT' is distinguished from its male parent 'Jason Blue' (not patented) in the flower color, 'Jason Blue' having a silvery blue eye not found in 'ENLIGHTENMENT'.

The closest commercial cultivar to 'ENLIGHTENMENT' known to the inventor is 'Sun Shower' (not patented). However, in side-by-side comparisons conducted in Webster, Tex., plants of 'ENLIGHTENMENT' differ from plants of 'Sun Shower' in the following characteristics:

1. Flowers of the new *hibiscus* have a different color pattern than flowers on the cultivar Sun Shower;
2. Plants of the new *Hibiscus* are easier to clone via rooting than plants of the cultivar Sun Shower; and
3. Plants of the new *Hibiscus* possess an improved growth habit over that of the cultivar 'Sun Shower', which is usually sprawling and difficult to maintain in production and as a landscape plant.

'Enlightenment' also has a sibling, namely the *Hibiscus rosa-sinensis* 'Hollywood' (U.S. Plant patent application Ser. No. 11/213,646). Although these plants are closely related, they both have distinctive flower coloration. Specifically, the two flowers differ in the following ways:

1. 'Enlightenment' has a pink center, 'Hollywood' does not;
2. The dominant colors on 'Enlightenment's' flower are pink, orange and yellow, and for 'Hollywood' it is red, orange and yellow; and
3. 'Enlightenment' has white flecks throughout the center while 'Hollywood' does not.

BRIEF DESCRIPTION OF THE DRAWINGS

The accompanying illustrations show a specimen of the new cultivar in a photographic illustration as true to color as is reasonably possible to make in an illustration of this character. Color values in the illustrations may differ slightly from the color values cited in the detailed botanical description, which accurately describes the actual colors of the new *Hibiscus*.

DETAILED DESCRIPTION OF THE INVENTION

Figure 1:
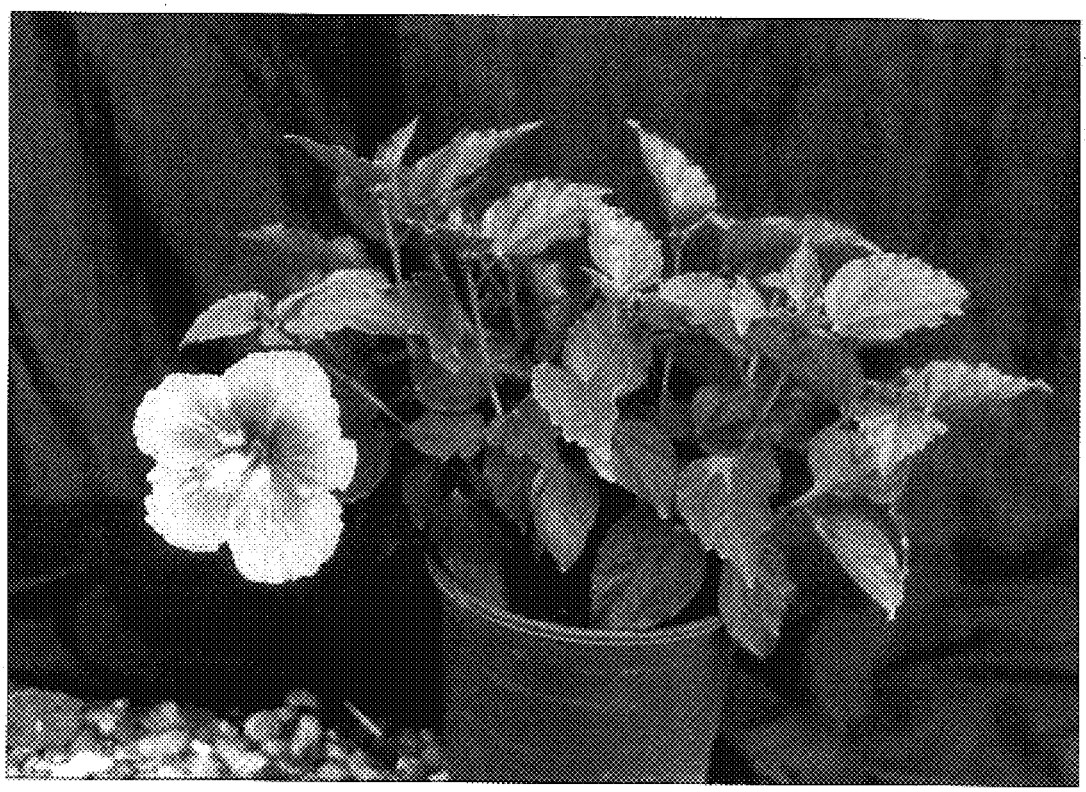
FIG. 1 illustrates a side perspective view of a typical plant of 'ENLIGHTENMENT'.
Figure 2:
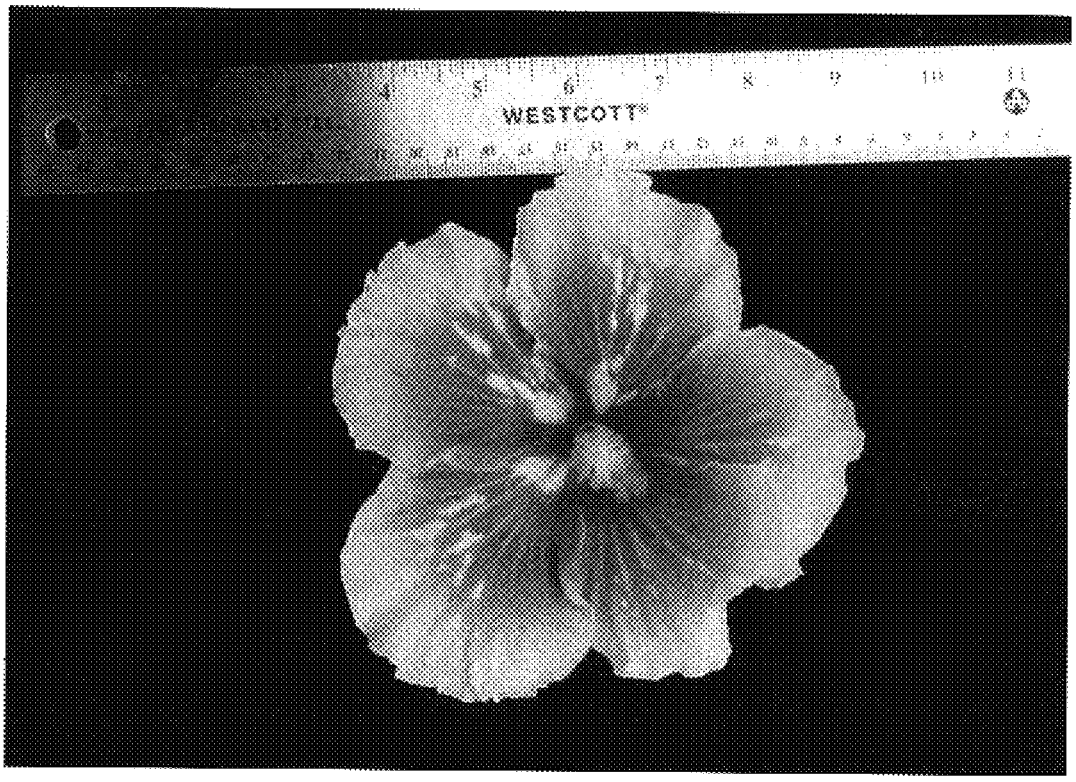
FIG. 2 illustrates the scale of a typical flower of 'ENLIGHTENMENT'.
Figure 3:
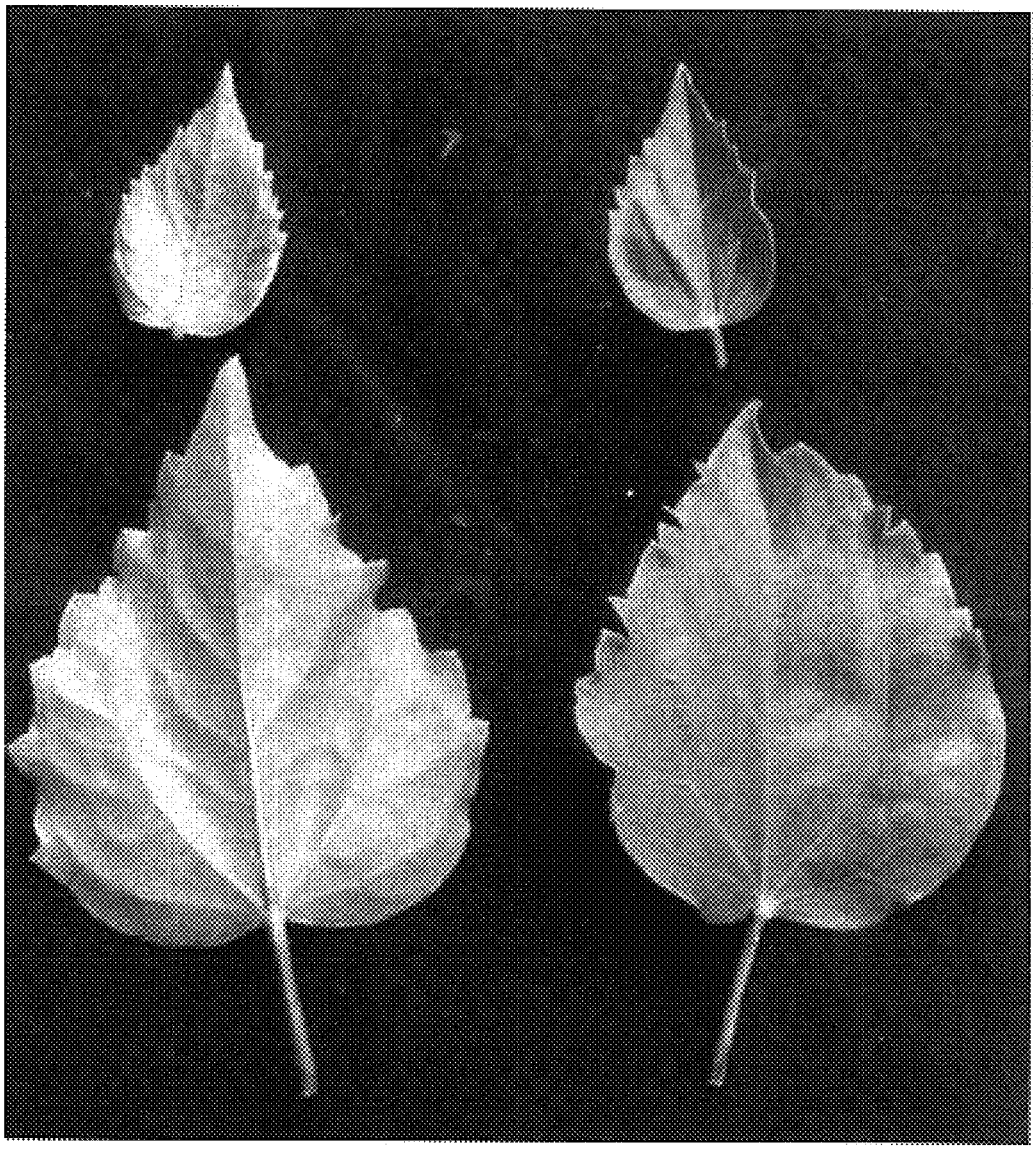
FIG. 3 illustrates the typical young to mature foliage of 'ENLIGHTENMENT'; the abaxial and adaxial surfaces are shown at each stage.
Figure 4:
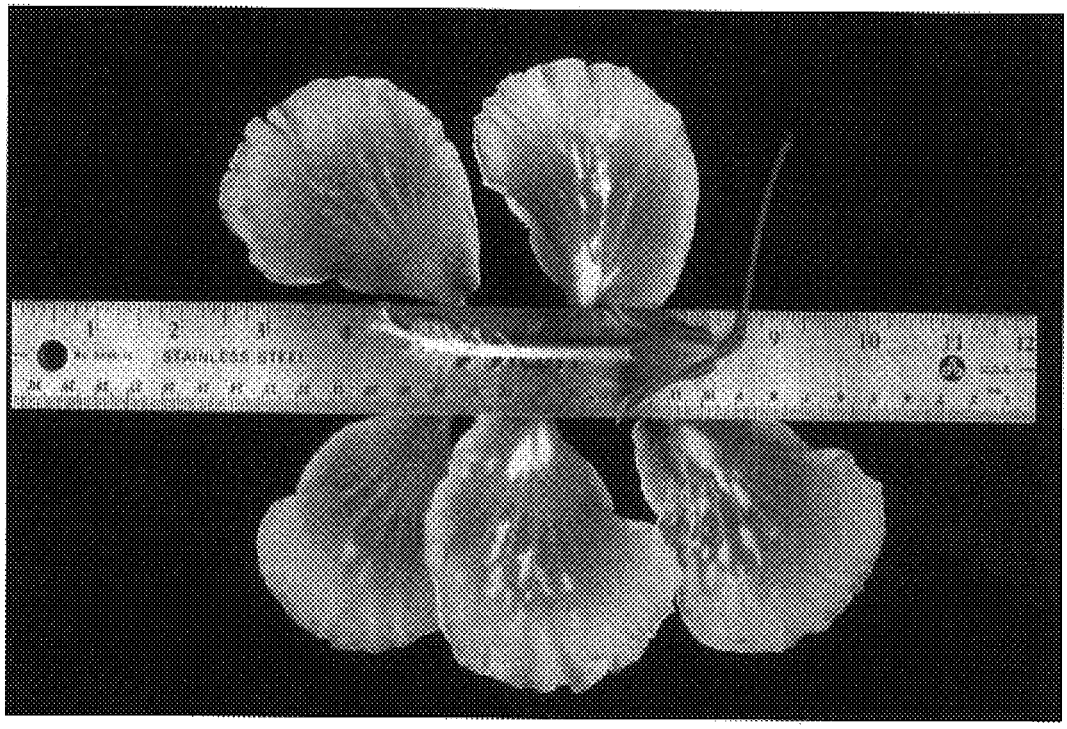
FIG. 4 illustrates a dissected flower of 'ENLIGHTENMENT', including shape and size of petals and characteristics of the reproductive structures.

'ENLIGHTENMENT' has not been observed under all possible environmental, cultural and light conditions. The following observations and descriptions are of plants grown in Fulshear, Tex., in April 2005, under polypropylene shadecloth providing a 30 percent light reduction, and under conditions which closely approximate commercial production. Plants described were approximately one year old.

In this description, color references are to The Royal Horticultural Society Colour Chart (4th Edition) and terminology used in the color descriptions herein refers to plate numbers in this color chart. Phenotypic expression may vary with light intensity, cultural and environmental conditions.

Classification:

*Botanical.*—*Hibiscus rosa-sinensis* 'ENLIGHTENMENT'.

*Parentage.*—Female or Seed Parent: *Hibiscus rosa-sinensis* 'Georgia's Pearl'. Male or Pollen Parent: *Hibiscus rosa-sinensis* 'Jason Blue'.

*Propagation.*—By cuttings.

*Time to initiate rooting.*—Approximately 14 to 21 days at 21–24° C.

*Time to develop roots.*—Approximately 42 to 56 days at 21–24° C.

*Root description.*—Fine to medium; fibrous; freely branching.

Plant:

*Size.*—Height: Approximately 40–50 cm in a #2 pot (from soil level to top of flowers). Diameter/Spread: Approximately 40–50 cm in a #2 pot.

*Form and growth habit.*—Perennial, evergreen shrub; mostly upright and somewhat spreading.

*Branching.*—Freely branching, about 4 to 8 lateral branches develop after pinching. Lateral Branches: Approximately 19 cm long and 4 mm in diameter. Color: Young — 146B. Mature — 199D. Internode Length: Approximately 4 cm.

Leaf:

*Shape.*—Cordate. Apex: Acute. Base: Cordate.

*Leaf size.*—Approximately 11 cm long and 9 cm wide.

*Arrangement.*—Alternate, single, symmetrical.

*Margin.*—Crenate.

*Aspect.*—Undulate.

*Texture.*—Glabrous, shiny.

*Coloration.*—Young Foliage Upper side: Near Yellow-Green Group 146A. Under side: Near Yellow-Green Group 146B. Mature Foliage Upper side: Near Yellow-Green Group 147A. Under side: Near Yellow-Green Group 147B.

*Petioles.*—Size: Approximately 4 cm in length; approximately 2 mm in diameter. Coloration: Near Yellow-Green Group 147A. Texture: Smooth.

Inflorescence:

*Bloom period.*—Typically year-round under subtropical and tropical conditions.

*Flower arrangement.*—Arranged singly at terminal leaf axils; free flowering with 3 to 4 flower buds and/or open flowers per terminal apex; flowers face upright and slightly outward.

*Flower appearance.*—Ruffled multicolored flower with a pink center, orange halo and yellow edges with white flecks throughout the center; flowers are open for about two days before closing; flowers persistent.

*Flower diameter.*—Approximately 15 cm.

*Flower depth.*—When placed on a horizontal plane, the flower extends 8 cm above the surface, with the ruffled petals extending 2 cm above the surface.

*Buds (just prior to showing color).*—Rate of Opening: Approximately 1 or 2 days, depending on temperature. Shape: Elliptic. Length: Approximately 3 cm. Diameter: Approximately 1.2 cm. Color: Near Yellow-Green Group146B.

*Fragrance.*—None noted.

*Petals.*—Number/Arrangement: Corolla consists of 5 overlapping petals. Shape: Spatulate with rounded apex. Size: Approximately 8 cm long and 7 cm wide. Margin: Entire, but ruffled. Texture: Smooth. Base Descriptor: Oblique. Color Upper Surface: Edges are near Yellow Group, between 9A and 9B, transitioning to a halo near Orange Group, between N25B and N25C, with a center near Red Group 55A. There are flecks of white, near N155A, present in the center. Lower Surface: Majority of the lower surface is near Yellow Group between 9C and 9D, fading to near White Group 155B at the base of the petal.

*Sepals.*—Number/Arrangement: 5 sepals fused into a star-shaped calyx. Shape: Linear with acuminate apices. Margin: Entire. Color: Near Yellow-Green Group 146B.

*Peduncles.*—Length: Approximately 4 cm. Diameter: Approximately 2 mm. Angle: Upright to about 45 degrees. Strength: Strong, flexible. Color: Near Yellow-Green Group 146B.

Reproductive organs:

*Androecium.*—Stamens: Numerous; approximately 50. Stamen Length: Approximately 5 mm. Filament Color: Near White Group 155B. Anther Size: Approximately 1 mm long×1 mm wide. Pollen Amount: Abundant. Pollen Color: Near Yellow Group 14B.

*Gynoecium.*—Pistil Length: Approximately 7.5 cm. Stigma Appearance: Five, rounded. Stigma Diameter: Approximately 2 mm. Stigma Color: Near Orange Group 25A. Style Color: Lower half near Red Group, between 55A and 55C; upper half is near White Group 155B. Seed Production: Has not been observed.

Pests/diseases: Resistance to known *Hibiscus* diseases has not been observed on plants grown under conditions approximating commercial practices.

What is claimed is:

1. A new *Hibiscus rosa-sinensis* plant named 'ENLIGHTENMENT', substantially as shown and described.

* * * * *